United States Patent
Amiot et al.

(10) Patent No.: US 7,938,777 B2
(45) Date of Patent: May 10, 2011

(54) NON-INVASIVE TRACKING OF BONES FOR SURGERY

(75) Inventors: Louis-Philippe Amiot, Hampstead (CA); Eric Szmutny, Philipsburg (CA); François Paradis, Boucherville (CA)

(73) Assignee: Orthosoft Inc., Montreal (CA)

( * ) Notice: Subject to any disclaimer, the term of this patent is extended or adjusted under 35 U.S.C. 154(b) by 862 days.

(21) Appl. No.: 11/878,022

(22) Filed: Jul. 20, 2007

(65) Prior Publication Data

US 2008/0021310 A1   Jan. 24, 2008

Related U.S. Application Data

(60) Provisional application No. 60/832,151, filed on Jul. 21, 2006.

(51) Int. Cl.
*A61B 8/00* (2006.01)
(52) U.S. Cl. ...................................................... 600/437
(58) Field of Classification Search ............. 600/426, 600/437
See application file for complete search history.

(56) References Cited

U.S. PATENT DOCUMENTS

| | | | |
|---|---|---|---|
| 1,941,468 A * | 1/1934 | Gilbert .............................. 2/93 |
| 3,895,525 A | 7/1975 | Eichelberger et al. | |
| 4,305,296 A | 12/1981 | Green et al. | |
| 5,197,476 A | 3/1993 | Nowacki et al. | |
| 6,159,152 A | 12/2000 | Sumanaweera et al. | |
| 6,190,320 B1 | 2/2001 | Lelong | |
| 6,314,310 B1 * | 11/2001 | Ben-Haim et al. ............ 600/424 |
| 6,390,982 B1 | 5/2002 | Bova et al. | |
| 6,529,758 B2 | 3/2003 | Shahidi | |
| 6,585,731 B1 | 7/2003 | Rattner et al. | |
| 6,702,746 B1 | 3/2004 | Srouji | |
| 6,725,082 B2 | 4/2004 | Sati et al. | |
| 6,746,402 B2 | 6/2004 | Ustuner | |
| 6,768,496 B2 | 7/2004 | Bieger et al. | |
| 2002/0065461 A1 * | 5/2002 | Cosman ....................... 600/426 |
| 2002/0087101 A1 * | 7/2002 | Barrick et al. ................ 600/587 |
| 2003/0018255 A1 | 1/2003 | Martin et al. | |
| 2003/0036762 A1 | 2/2003 | Kerr et al. | |
| 2004/0068260 A1 | 4/2004 | Cossette et al. | |
| 2005/0015022 A1 | 1/2005 | Richard et al. | |
| 2005/0101866 A1 | 5/2005 | Goodwin | |
| 2005/0143676 A1 | 6/2005 | De Guise et al. | |
| 2005/0238216 A1 | 10/2005 | Yoden | |
| 2007/0100325 A1 | 5/2007 | Jutras et al. | |
| 2007/0225595 A1 * | 9/2007 | Malackowski et al. ....... 600/424 |

FOREIGN PATENT DOCUMENTS

| | | |
|---|---|---|
| DE | 4231101 A1 | 3/1994 |
| DE | 10136737 A1 | 2/2003 |
| DE | 10346615 A1 * | 5/2005 |
| EP | 0353209 A1 | 1/1990 |
| EP | 1161194 A1 | 12/2001 |
| EP | 0966691 B1 | 8/2005 |
| JP | 2005160704 A * | 6/2005 |

(Continued)

*Primary Examiner* — Tse Chen
*Assistant Examiner* — Jacqueline Cheng
(74) *Attorney, Agent, or Firm* — Ogilvy Renault LLP

(57) ABSTRACT

There is described a device for use with a position sensing system for tracking a bone in a reference coordinate system, the device comprising a fabric removably and non-invasively attachable to a bone and having a plurality of reference markers distributed thereon, the reference markers being one of passive and active devices recognized by the position sensing system and positioned and oriented in the reference coordinate system with respect to a fixed reference.

9 Claims, 7 Drawing Sheets

FOREIGN PATENT DOCUMENTS

| | | |
|---|---|---|
| WO | WO 0224075 A1 | 3/2002 |
| WO | WO 0224094 A2 | 3/2002 |
| WO | WO 03009772 A1 | 2/2003 |
| WO | WO 2004/014488 A1 | 2/2004 |
| WO | WO 2004/016178 A2 | 2/2004 |
| WO | WO 2004/030559 A1 | 4/2004 |
| WO | WO 2004/069073 A2 | 8/2004 |
| WO | WO 2005/039391 A2 | 5/2005 |
| WO | WO 2005/043319 A2 | 5/2005 |
| WO | WO 2005/092198 A1 | 10/2005 |
| WO | WO 2006//079211 A1 | 8/2006 |
| WO | WO 2006/128301 A1 | 12/2006 |

* cited by examiner

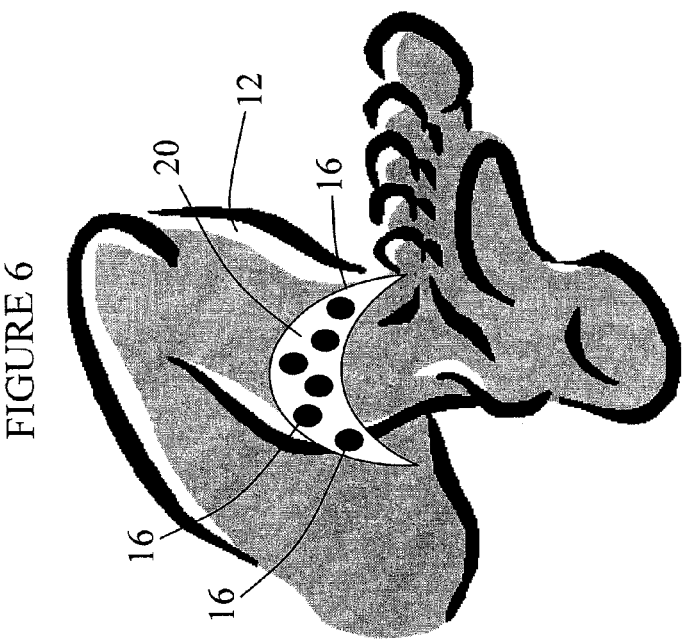
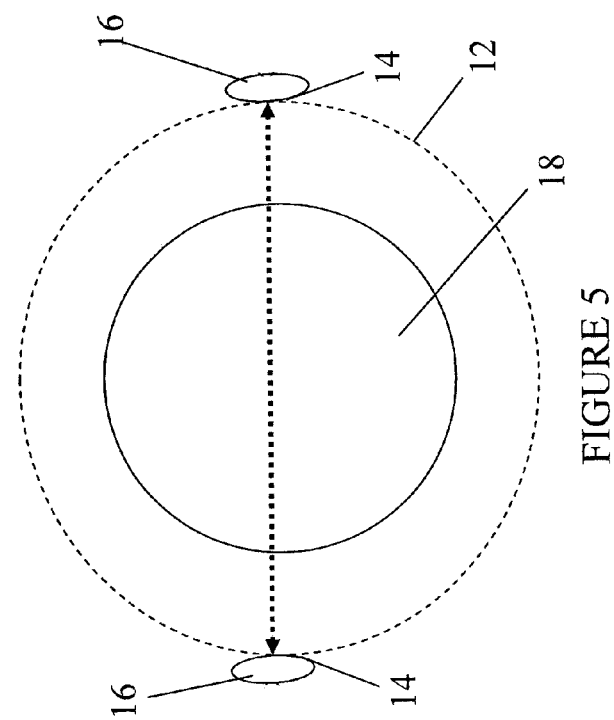

NON-INVASIVE TRACKING OF BONES FOR SURGERY

CROSS-REFERENCE TO RELATED APPLICATIONS

The present application claims priority of U.S. Provisional Patent Application No. 60/832,151 filed on Jul. 21, 2006, the contents of which are hereby incorporated by reference, and is related to U.S. patent application of the same title filed concurrently herewith.

TECHNICAL FIELD

The present invention relates to the field of computer-assisted medical procedures, and more specifically, to bone tracking and positioning in computer-assisted surgery (CAS) systems.

BACKGROUND

Computer-assisted surgery (CAS) makes use of references fixed to the patient using pins inserted into the bones of the limbs or the pelvis. These pins, inserted into the bones before or during the surgery, are of different diameter sizes and can cause pain after the surgery. They are an extra step to the surgery, exclusively because of the navigation system. Also, the insertions of the pins into the bone may cause weaknesses of the bone that can then more easily be fractured. Infections may also occur as for any entry point at surgery.

Furthermore, the length of the pins is sometimes obtrusive to the surgeon who may cut them to a length better adapted to his movement during the surgery. The cut is also perceived as an extra annoying step; its end may be sharp and hazardous to the personnel working around the surgery table.

The pins are time-consuming and invasive. Therefore, there is a need for an improvement in this area.

SUMMARY

The systems and methods described herein reduce the invasiveness and the time required when using pins in order to reference the bones of a patient during surgery.

In accordance with a first broad aspect of the present invention, there is provided a method for determining a position and orientation of a bone in space, the method comprising: removably attaching in a non-invasive manner at least three base units to a skin surface covering the bone, each of the base units having a reference marker attached thereto; measuring a distance between each of the base units and the bone; registering position and orientation readings of the reference markers with respect to a fixed reference in the reference coordinate system; and determining the position and orientation of the bone using the position and orientation of the reference markers and the distance between the base units and the bone.

The base units can be attached using a non-toxic adhesive, or provided on a fabric, such as a sock, belt, underwear, shorts, or any other type of apparel that can be worn on the body at the appropriate location. The ultrasound can be integrated inside the base units, or an external probe can be applied to each base unit to determine the distance from the skin surface to the bone.

In accordance with a second broad aspect of the present invention, there is provided a method for tracking a bone in a reference coordinate system, the method comprising: removably attaching in a non-invasive manner a piece of fabric around a bone, the fabric having a plurality of reference markers distributed thereon; registering position and orientation readings of the reference markers with respect to a fixed reference in the reference coordinate system; and determining a position and orientation of the bone using the readings.

The piece of fabric can be anything that can be attached to the body, such as a sock or belt. The reference markers can be optical, Radio Frequency (RF), (electro)magnetic, ultrasound, or any other known type of passive or active reference markers used in computer assisted surgeries.

In accordance with a third broad aspect of the present invention, there is provided a system for determining a position and orientation of a bone in space, the system comprising: a set of at least three base units removably and non-invasively attachable to a skin surface covering a bone, each of the base units having a reference marker attached thereto; at least one ultrasound device adapted to emit an ultrasound wave, receive an echo of the ultrasound wave off of a surface, and record a time measurement for the echo; a fixed reference positioned in the reference coordinate system and used to identify a position of the reference markers in the reference coordinate system; a position sensing device adapted to register position and orientation readings of the reference markers in a reference-coordinate system; and a processing unit receiving the position and orientation readings and the time measurement, translating the time measurement into a distance measurement, and determining the position and orientation of the bone.

In accordance with a fourth broad aspect of the present invention, there is provided a system for tracking a bone in a reference coordinate system, the system comprising: a fabric removably and non-invasively attachable to a bone and having a plurality of reference markers distributed thereon; a fixed reference positioned in the reference coordinate system and used to identify a position of the reference markers in the reference coordinate system; a position sensing device adapted to register position and orientation readings of the reference markers; and a processing unit receiving the position and orientation readings and determining a position and orientation of the bone.

In accordance with a fifth broad aspect of the present invention, there is provided a device for use with a position sensing system to register position and orientation in a reference-coordinate system, the device comprising a set of at least three base units removably and non-invasively attachable to a skin surface covering a bone, each of the base units having a reference marker attached thereto, the reference markers being one of passive and active devices recognized by the position sensing system and positioned and oriented in the reference coordinate system with respect to a fixed reference, the base units adapted to measure a distance between the skin surface and the bone in conjunction with an ultrasound component.

In accordance with a sixth broad aspect of the present invention, there is provided a device for use with a position sensing system for tracking a bone in a reference coordinate system, the device comprising a fabric removably and non-invasively attachable to a bone and having a plurality of reference markers distributed thereon, the reference markers being one of passive and active devices recognized by the position sensing system and positioned and oriented in the reference coordinate system with respect to a fixed reference.

In this specification, the term "reference marker" is intended to mean an active or passive marker, such as an emitter or a reflector. The term "fixed reference" may also refer to any active or passive device, with a known position in the reference coordinate system.

BRIEF DESCRIPTION OF THE DRAWINGS

Further features and advantages of the present invention will become apparent from the following detailed description, taken in combination with the appended drawings, in which:

FIG. 5 is a cross-sectional view of an elongated bone, such as a femur, with a single pair of reference markers around the bone;

FIG. 6 is an illustration showing a piece of fabric with reference markers thereon attached to a leg;

It will be noted that throughout the appended drawings, like features are identified by like reference numerals.

DETAILED DESCRIPTION

Figure 1:
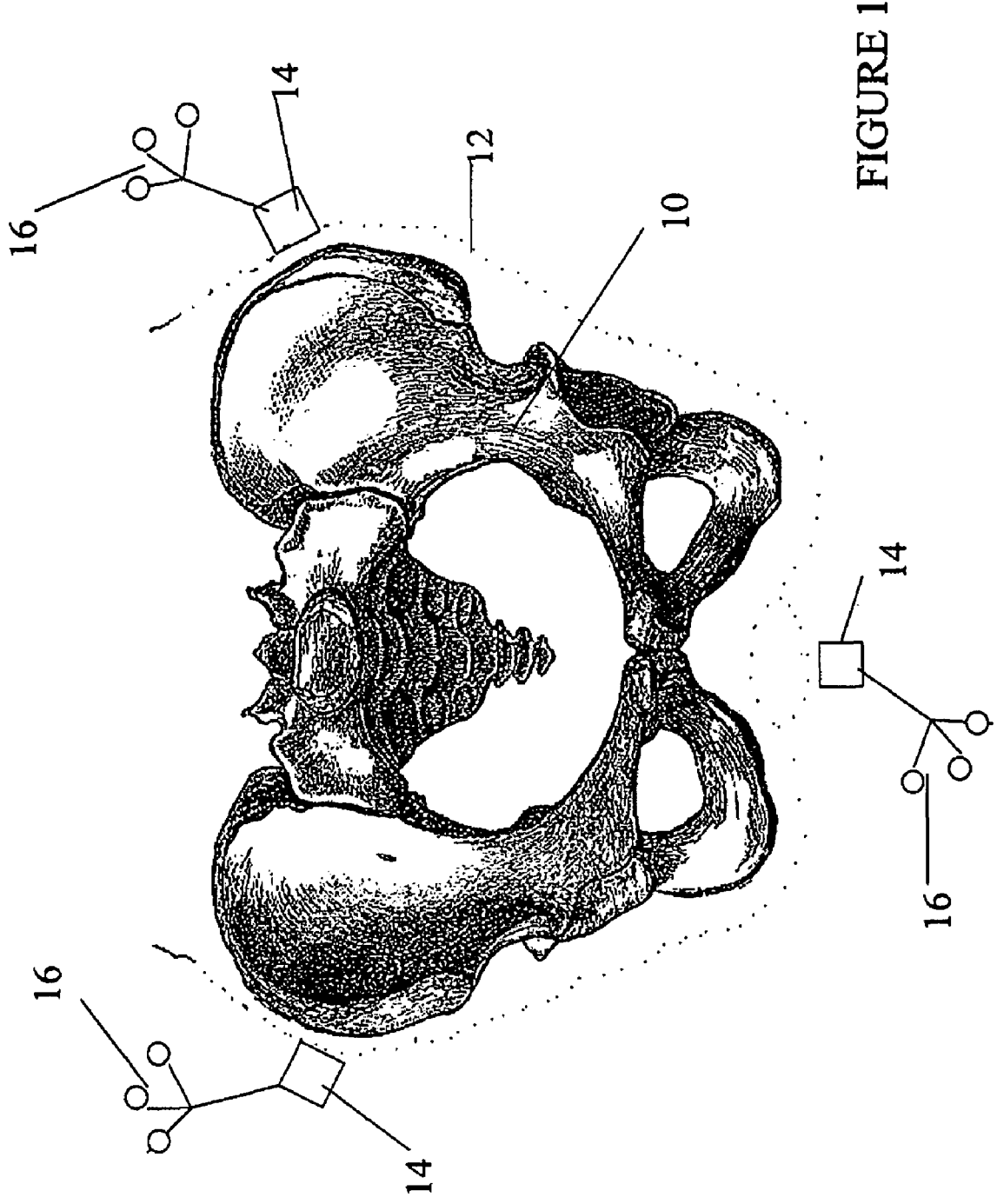
FIG. 1 is a front view of a pelvic bone with three base units attached on the skin surface.

FIG. 1 illustrates a pelvic bone 10 covered by the skin 12. Three base units 14 are attached to the skin 12. The base units 14 may be attached using a medical adhesive, i.e. non-toxic for the patient, or it can be provided on a piece of fabric that is worn by the patient during the surgery. For example, a pair of snug-fitting shorts or underwear (undergarment) having the base units 14 attached thereto are worn by the patient.

One base unit 14 is attached to each crest of the hip (anterior superior iliac spines), and a third base unit 14 is attached to the pubis area (pubic symphysis) of the pelvis. These locations on the pelvis are chosen for having minimum distance between the out-skin 12 and the bone 10. The base units 14 may be positioned at other locations on the pelvic bone, without being restricted to these locations in particular.

Reference markers 16 are present in/on each base unit. These reference markers 16 may be active or passive, optical, RF, (electro-)magnetic, or other. In FIG. 1, optical reflective reference markers are illustrated. These three points define the pelvic coordinate system. The position sensing system used with the CAS system will register the position and orientation in space of the pelvic bone with respect to either pre-operative images of the patient, such as CT-scans, fluoroscopy, x-rays, etc, or with respect to any type of intra-operative reconstruction of the bones illustrated on an interactive display device. A fixed reference present in the coordinate system and having a known position is used to position and orient the pelvic bone in space.

In one embodiment of the present invention, the distance of each base unit 14 on the out-skin 12 to the bone 10 is measured using an ultrasound probe that is applied to each base unit 14. The ultrasound, which is a transducer, emits an ultrasound wave and measures the time it takes for the wave to echo off of a hard surface (such as bone) and return to the transducer face. Using the known speed of the ultrasound wave, the time measurement is translated into a distance measurement between the base unit and the bone located below the surface of the skin. In another embodiment, an ultrasound device is integrated into each base unit 14. The measurement is done by either triggering it manually, or automatically. In one embodiment, the measurement is repeated at regular intervals. The measurements are constantly being transferred to the CAS and the position and orientation of the bone 10 in space is updated. The measurement of the distance from the base unit to the bone may also be done using alternative imaging means, such as fluoroscopy. A metal reference is positioned on the skin surface and used with a fluoroscopy system to identify the bone surface. It is possible to make the measurement from the metal reference to the bone surface on the fluoroscopic image Once the distance between the base unit 14 and the bone 10 is known, an estimation of the possible displacement of the base unit 14 on the out-skin relative to the bone 10 can be done and the bone can then be registered to the reference system. In the case of the integrated ultrasound device within each base unit 14, it becomes possible to measure in real-time variations in distance between the base units 14 and the bone 10 during the surgery.

Figure 2:
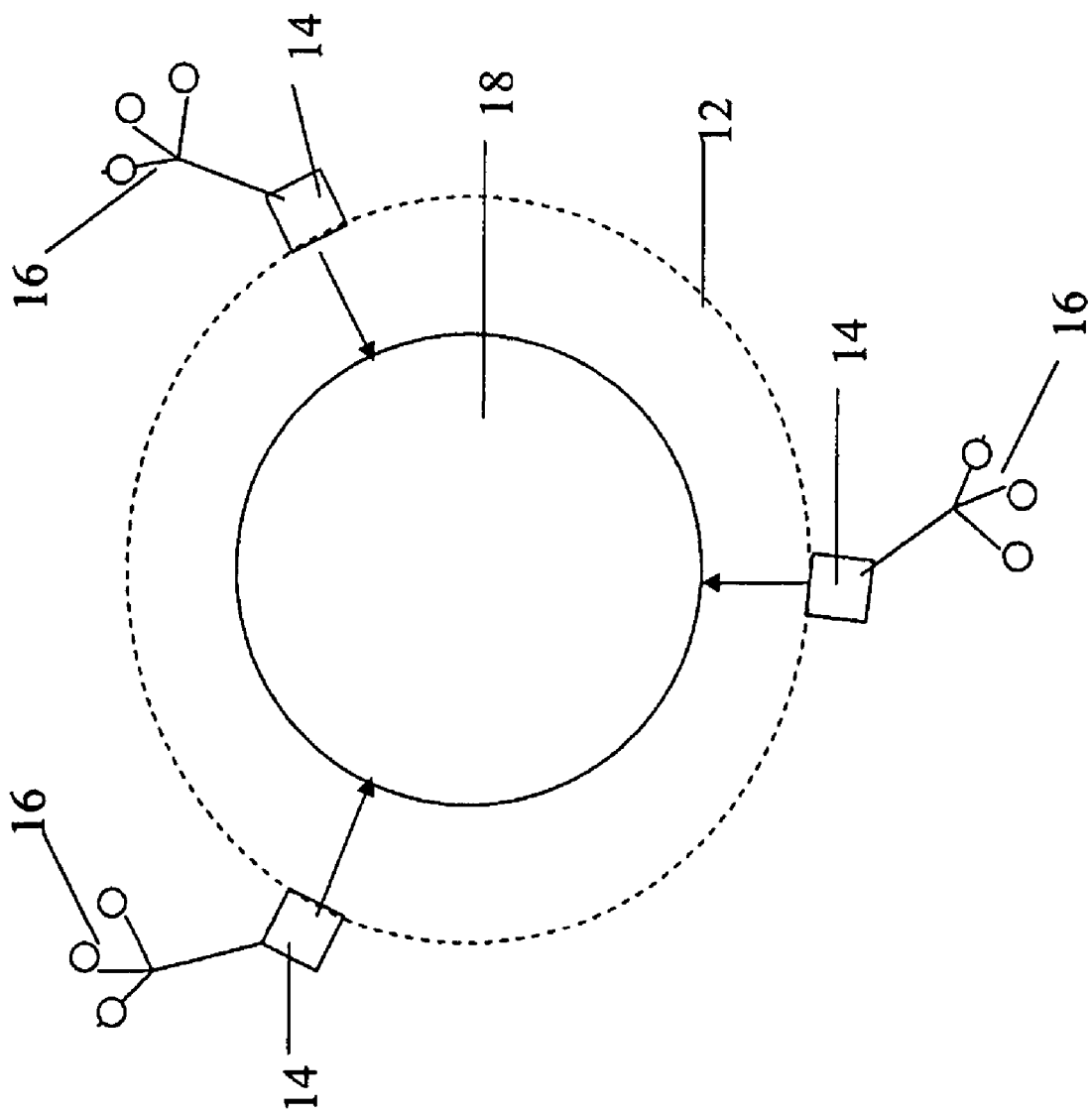
FIG. 2 is a cross-sectional view of an elongated bone, such as a femur, with three base units attached on the skin surface.

FIG. 2 is a cross-sectional view of a bone 18, such as a femur, a tibia, or any other bone having an elongated form. The base units 14 are positioned around the bone 18 on the out-skin 12. Similarly to the case of the pelvis 10, the base units 14 may be glued onto the body 18, or a piece of fabric having the base units 14 attached thereto is placed on the body in a snug-fitting manner. For a limb, a sleeve, sock, or belt may be used. The base units 14, each having reference markers 16 are therefore distributed around the bone. If the reference markers 16 are of the optical type, than only the reference markers 16 in the line-of-sight of the position sensing system will be registered. In the case of a limb, this may mean that only half of the reference markers are visible. The other half can be extrapolated using the readings obtained from the visible markers. For other types of reference markers, such as RF emitters, all reference markers on the bone will generate a reading in order to register the position and orientation of the bone in space.

When tracking the orientation and position of an elongated bone, the problems encountered due to cutaneous movement can be resolved by placing a single reference marker directly on the bone at the beginning of the surgery. If that reference marker is an ultrasound, the sound emitted by the reference marker can be captured by the base units on the skin. Therefore, the invasive pins are replaced by an ultrasound link, and the only invasive part is the incision that would have been made in any case.

Figure 3:
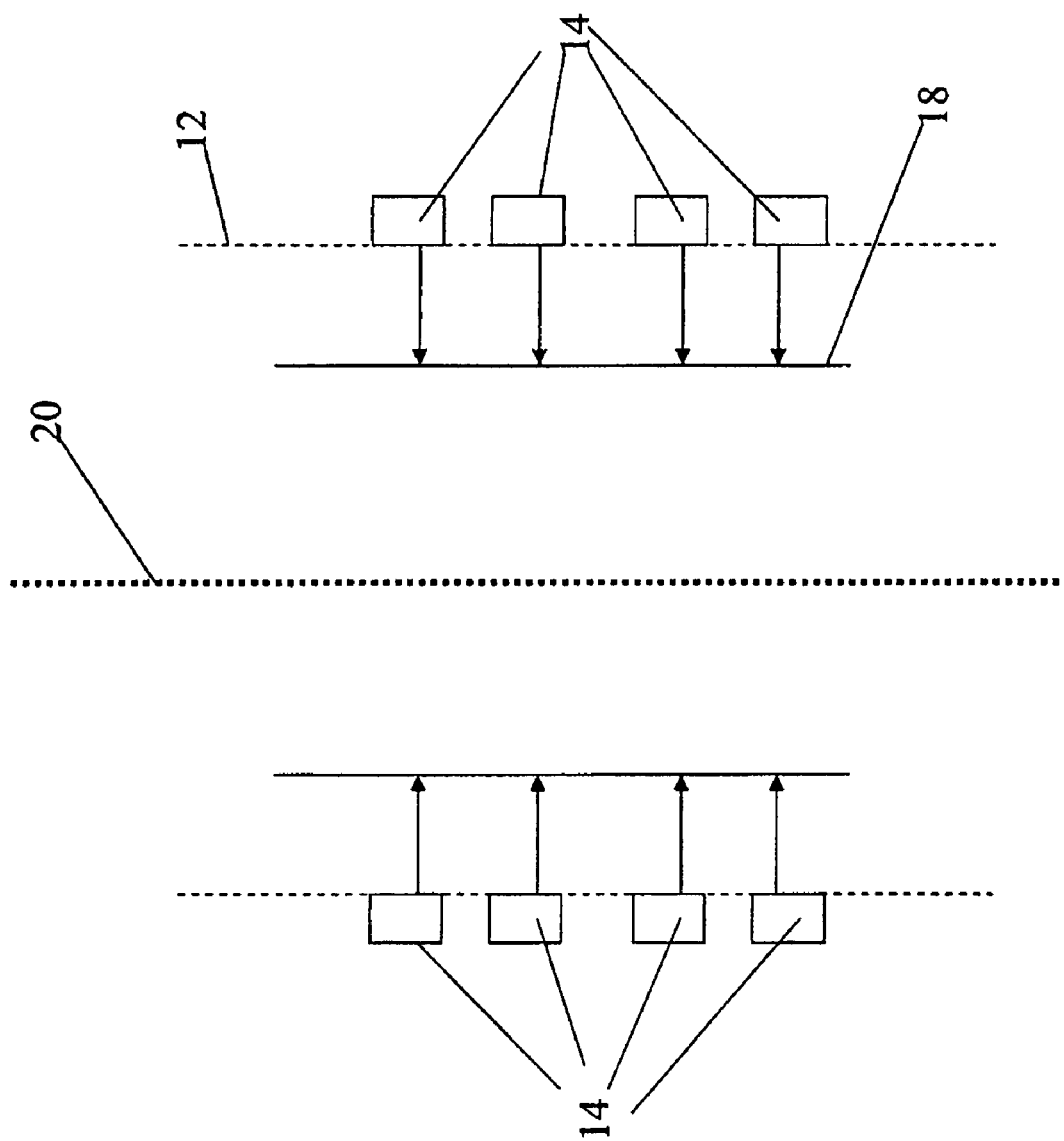
FIG. 3 is a front view of an elongated bone, such as a femur, with multiple pairs of base units provided thereon.

FIG. 3 is a front view of the bone shown in cross-section in FIG. 2. The base units 14, including the reference markers (not shown), are placed on the out-skin 12 of the bone 18. The distance between the bone 18 and the out-skin 12 is measured using ultrasound. The possible variation of distance between the base and the bone during the surgery can be measured, either once at the beginning or in real-time during the surgery.

Figure 4:
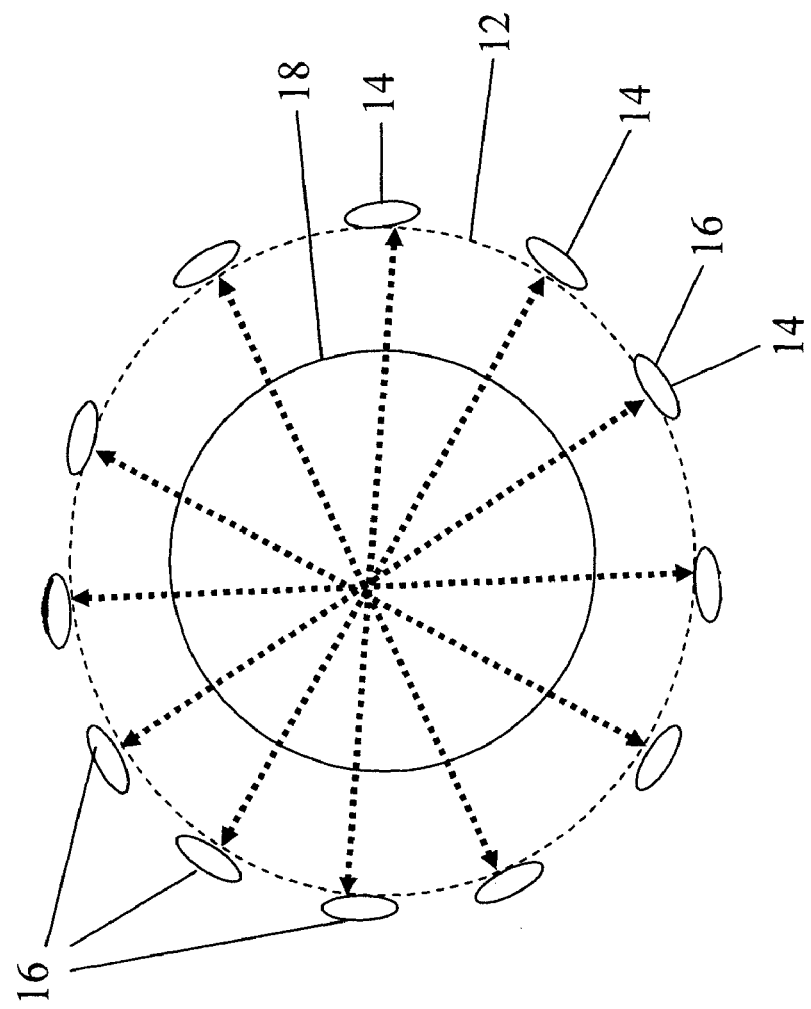
FIG. 4 is a cross-sectional view of an elongated bone, such as a femur, with a plurality of reference markers around the bone.

The anatomical axis 20 of the bone 18 can also be determined. The ultrasound probe is not necessary to determine the anatomical axis 20. Pairs of reference markers 16 on the out-skin 12 are positioned such that they are substantially facing each other, as illustrated in FIG. 4. The mid-point between the measured position of each marker in a pair will constitute a point on the anatomical axis 20.

A minimum of one pair, i.e. two reference markers 16 face-to-face, is needed to determine the anatomical axis, as illustrated in FIG. 5, if used in combination with a single reference marker placed at a distal end of the bone. Alternatively, two pairs of reference markers positioned face-to-face could also be used to determine the anatomical axis 20 by providing at least two points on the axis 20.

In one embodiment of the present invention, a belt 20 having ultrasound emitters thereon is attached around a leg of a patient, as illustrated in FIG. 6. A fixed reference is provided in the reference system, for example on a cutting block positioned on the knee, or attached to the pelvis bone (not shown). The reference markers on the belt 20 are referenced to the fixed reference, for example by using a pointer and applying it to the reference markers on the belt 20. This can also be done automatically without a pointer. The ultrasound emitters measure the distance between the skin and the bone, and the position and orientation of the bone in space is determined.

In another embodiment, a belt having reference markers (not necessarily ultrasound emitters) is attached around a leg of the patient. The reference markers are positioned such that there are pairs of markers substantially facing each other. The anatomical axis of the bone is determined by locating the middle point between a pair of markers and forming a line from these points along the bone. The position of the belt in space is determined using the reference markers on the belt. At least one pair of reference markers are needed to determine the anatomical axis, if the reading from a single reference marker provides a position from which more than one point on a line can be determined.

Figure 7:
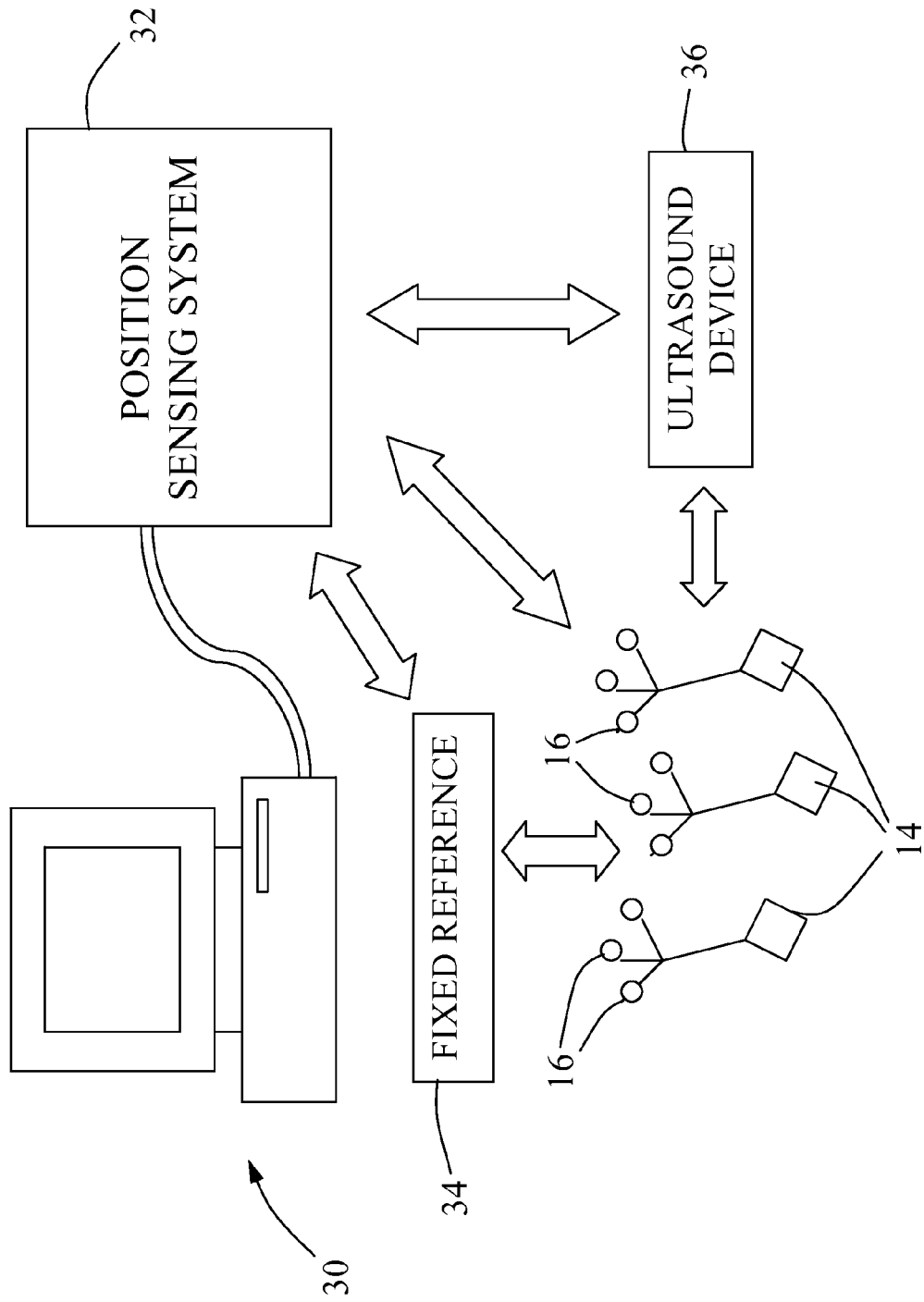
FIG. 7 is a block diagram of an embodiment of a system of the present invention used with a set of base units.

FIG. 7 illustrates a system in accordance with one embodiment of the present invention. A processing unit 30 and a position sensing system 32 are coupled with a set of at least three base units 14, each base unit 14 having a reference marker 16 thereon. The reference markers 16 on the base units 14 are used to position the bone within a reference coordinate system. The position sensing system, as is known in the art, will use either active or passive devices as markers. The orientation and position of the bone in space can be determined using the information obtained from the reference markers 16 and using the known position of the fixed reference 34 in the coordinate system. In addition, an ultrasound device 36 is used to measure the distance between the surface of the skin and the bone underneath the surface. By updating this measurement, a more precise positioning of the bone is obtained.

The base units may be provided with a non-toxic adhesive on a surface and stuck directly onto the skin. Alternatively, a fabric mounted with the base units is attached to the skin, as is described above. The ultrasound device is either integrated into each base unit, or used externally to the base units by applying it manually to each base unit, in the form of a probe, for example.

Figure 8:
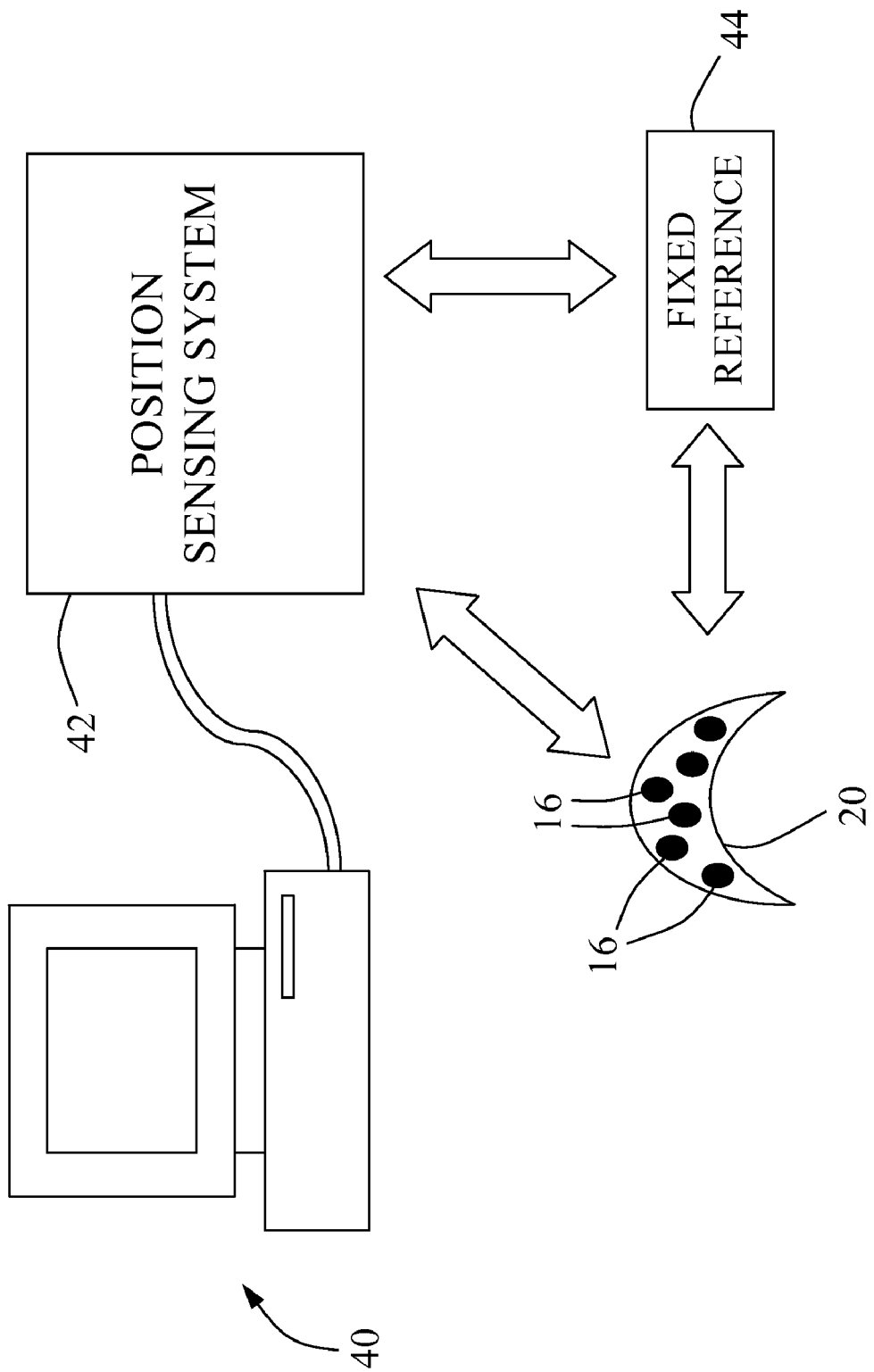
FIG. 8 is a block diagram of an embodiment of a system of the present invention used with a fabric having reference markers attached thereto.

An alternative embodiment of the system is illustrated in FIG. 8. A processor 40 and a position sensing system 42 are coupled to a fabric 20 removably and non-invasively attachable to a bone and having a plurality of reference markers 16 distributed thereon, and a fixed reference 44 positioned in the reference coordinate system and used to identify a position and orientation of the reference markers in the reference coordinate system.

The reference markers 16 on the fabric 20 may be distributed on the fabric in a variety of ways. One such way is to have at least two reference markers substantially facing each other when the fabric is wrapped around a bone. One or more rows of pairs of markers can be provided on the fabric, as is illustrated in FIG. 5.

The processor is preferably a general purpose computer equipped with software that allows it to compute the location of a bone surface from the information obtained by the reference markers and ultrasound device. The results may be displayed on a screen or monitor to be visualized by a user or operator. The information may be used in conjunction with other known registration techniques to assist in pre-operative or intra-operative procedures. The components of the system may need to be calibrated using standard procedures known to the person skilled in the art.

While illustrated in the block diagrams as groups of discrete components communicating with each other via distinct data signal connections, it will be understood by those skilled in the art that the preferred embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present preferred embodiment. The embodiments of the invention described above are intended to be exemplary only. The scope of the invention is therefore intended to be limited solely by the scope of the appended claims.

We claim:

1. A method for tracking a bone in a reference coordinate system, the method comprising:
    removably attaching in a non-invasive manner a belt around a bone, said belt having a plurality of reference markers distributed thereon, and positioning at least two of said reference markers such that they are substantially facing each other when said belt is around said bone;
    registering without imagery position and orientation readings of said reference markers with respect to a fixed reference in said reference coordinate system;
    determining without imagery a position and orientation of said bone using said readings, including calculating an anatomical axis from readings of said reference markers on each side of said bone by determining a mid-point therebetween; and
    repeating said registering and said determining to update said position and orientation readings while tracking said bone.

2. A method as claimed in claim 1, wherein said removably attaching comprises positioning a plurality of pairs of facing reference markers along said anatomical bone to increase a precision reading of said anatomical axis.

3. A method as claimed in claim 2, wherein said reference markers are ultrasound emitters used to measure a distance between said belt and said bone.

4. A method as claimed in claim 1, wherein said registering position and orientation readings of said reference markers with respect to a fixed reference comprises referencing to a fixed reference attached to a separate bone.

5. A system for tracking a bone in a reference coordinate system, the system comprising:
    a fabric removably and non-invasively attachable around a bone and having a plurality of reference markers distributed thereon, said reference markers being distributed on said fabric such that at least two of said reference markers are substantially facing each other when said fabric is wrapped around said bone;
    a fixed reference positioned in said reference coordinate system and used to identify a position of said reference markers in said reference coordinate system;
    a position sensing device adapted to register position and orientation readings of said reference markers; and
    a processing unit receiving said position and orientation readings as continuously updated and determining a position and orientation of said bone without imagery using said readings, and wherein said processing unit is adapted to calculate an anatomical axis from said readings of said reference markers on each side of said bone by determining a mid-point therebetween.

6. A system as claimed in claim 5, wherein said reference markers are distributed to form at least two rows of pairs of facing reference markers.

7. A system as claimed in claim 5, wherein at least two of said plurality of reference markers are ultrasound devices adapted to emit an ultrasound wave and record an echo of said ultrasound wave off of a surface.

8. A system as claimed in claim 5, wherein said fixed reference is on a cutting block in said reference coordinate system.

9. A system as claimed in claim 5, wherein said fixed reference is on a pelvis bone in said reference coordinate system.

* * * * *

Disclaimer

7,938,777 B2 — Louis-Philippe Amiot, Hampstead (CA); Eric Szmutny, Philipsburg (CA); Francois Paradis, Boucherville (CA). NON-INVASIVE TRACKING OF BONES FOR SURGERY. Patent dated May 10, 2011. Disclaimer filed March 7, 2011, by the inventors.

Hereby enters the term of this patent not to exceed beyond the expiration date of serial number 11/878,021 filed July 20, 2007.

*(Official Gazette September 6, 2011)*